US012239831B2

(12) United States Patent
Sarkisyan et al.

(10) Patent No.: US 12,239,831 B2
(45) Date of Patent: *Mar. 4, 2025

(54) INTEGRATED ADJUSTABLE MULTI-PUMP MECHANICAL CIRCULATORY SUPPORT DEVICE

(71) Applicant: Drexel University, Philadelphia, PA (US)

(72) Inventors: Harutyun Sarkisyan, Rancho Cordova, CA (US); Amy L. Throckmorton, Cherry Hill, NJ (US)

(73) Assignee: DREXEL UNIVERSITY, Philadelphia, PA (US)

( * ) Notice: Subject to any disclaimer, the term of this patent is extended or adjusted under 35 U.S.C. 154(b) by 488 days.

This patent is subject to a terminal disclaimer.

(21) Appl. No.: 17/160,649

(22) Filed: Jan. 28, 2021

(65) Prior Publication Data
US 2021/0236801 A1    Aug. 5, 2021

Related U.S. Application Data

(60) Provisional application No. 62/967,865, filed on Jan. 30, 2020.

(51) Int. Cl.
| | |
|---|---|
| A61M 60/221 | (2021.01) |
| A61M 60/126 | (2021.01) |
| A61M 60/165 | (2021.01) |
| A61M 60/232 | (2021.01) |
| A61M 60/237 | (2021.01) |
| A61M 60/50  | (2021.01) |
| A61M 60/857 | (2021.01) |
| F04D 13/12  | (2006.01) |
| F04D 15/00  | (2006.01) |
| A61M 60/419 | (2021.01) |

(Continued)

(52) U.S. Cl.
CPC ........ *A61M 60/221* (2021.01); *A61M 60/126* (2021.01); *A61M 60/165* (2021.01); *A61M 60/232* (2021.01); *A61M 60/237* (2021.01); *A61M 60/50* (2021.01); *A61M 60/857* (2021.01); *F04D 13/12* (2013.01); *F04D 15/0011* (2013.01); *A61M 60/419* (2021.01); *A61M 60/82* (2021.01); *A61M 60/873* (2021.01)

(58) Field of Classification Search
CPC .............. A61M 60/221; A61M 60/232; A61M 60/237; F04D 13/12
See application file for complete search history.

(56) References Cited

U.S. PATENT DOCUMENTS

| | | | | |
|---|---|---|---|---|
| 4,611,578 A | * | 9/1986 | Heimes | A61M 60/554 417/19 |
| 5,263,979 A | * | 11/1993 | Isoyama | A61M 60/554 623/3.13 |
| 5,824,070 A | | 10/1998 | Jarvik | |

(Continued)

*Primary Examiner* — Rex R Holmes
*Assistant Examiner* — Jennifer L Ghand
(74) *Attorney, Agent, or Firm* — Howson & Howson LLP

(57) ABSTRACT

A mechanical circulatory support device is provided. The device has a housing containing separate first and second pumps. Each pump having an inlet, an outlet, and an impeller. The device also having a switching mechanism located within the housing and movable from a first position to a second position to divert blood flow within the housing to an inlet of one of the pumps and/or to bypass blood flow relative to one of the pumps within the housing.

16 Claims, 8 Drawing Sheets

(51) Int. Cl.
 *A61M 60/82* (2021.01)
 *A61M 60/873* (2021.01)

(56) References Cited

U.S. PATENT DOCUMENTS

| | | | |
|---|---|---|---|
| 5,938,412 A | 8/1999 | Izraelev | |
| 6,045,326 A | 4/2000 | Lecat | |
| 6,048,363 A * | 4/2000 | Nagyszalanczy | A61M 60/827 |
| | | | 623/3.13 |
| 8,777,832 B1 * | 7/2014 | Wang | A61M 60/216 |
| | | | 600/16 |
| 9,095,428 B2 | 8/2015 | Kabir et al. | |
| 9,689,403 B2 | 6/2017 | Fang et al. | |
| 9,919,085 B2 | 3/2018 | Throckmorton et al. | |
| 9,970,437 B2 | 5/2018 | Yuan | |
| 10,814,053 B2 | 10/2020 | Throckmorton et al. | |
| 2003/0032853 A1 * | 2/2003 | Korakianitis | A61M 60/894 |
| | | | 600/16 |
| 2005/0220636 A1 * | 10/2005 | Henein | A61M 60/232 |
| | | | 417/423.1 |
| 2009/0099498 A1 * | 4/2009 | Demers | A61M 60/531 |
| | | | 604/4.01 |
| 2016/0045654 A1 * | 2/2016 | Connor | A61M 60/894 |
| | | | 600/16 |
| 2016/0256619 A1 * | 9/2016 | Throckmorton | A61M 60/82 |
| 2018/0154056 A1 * | 6/2018 | Throckmorton | A61M 60/232 |
| 2021/0205599 A1 * | 7/2021 | Throckmorton | A61M 60/237 |

* cited by examiner

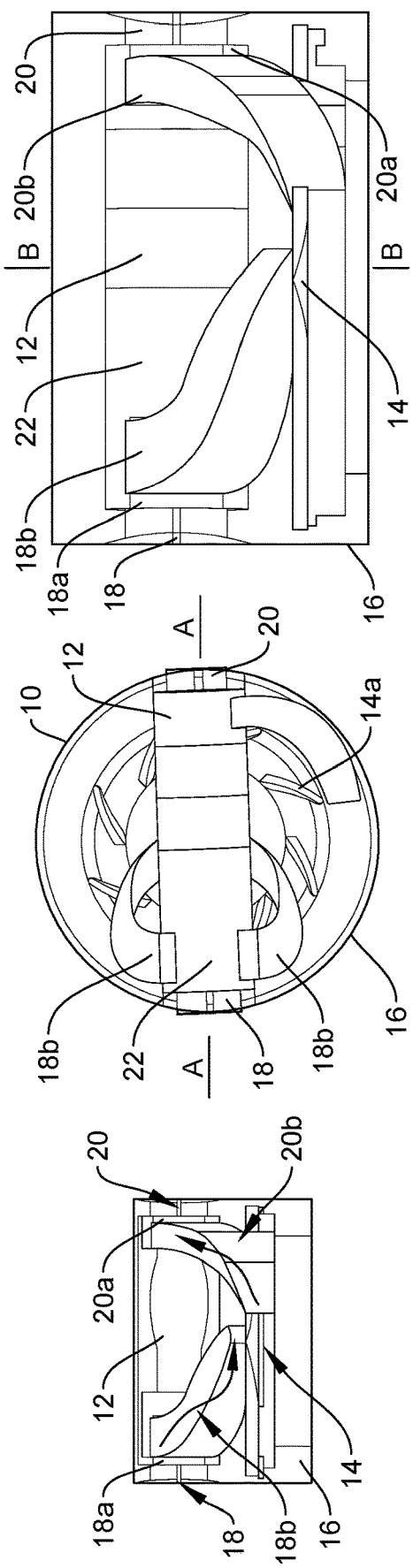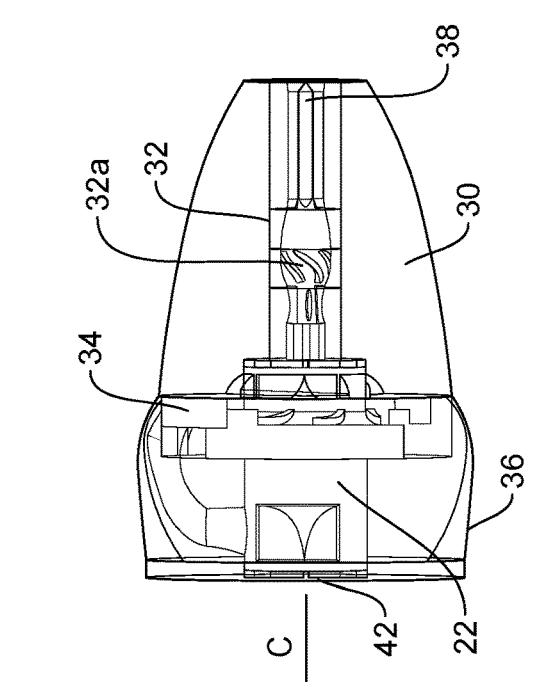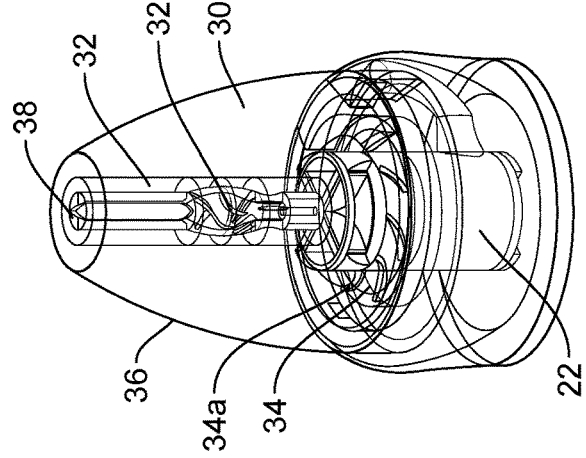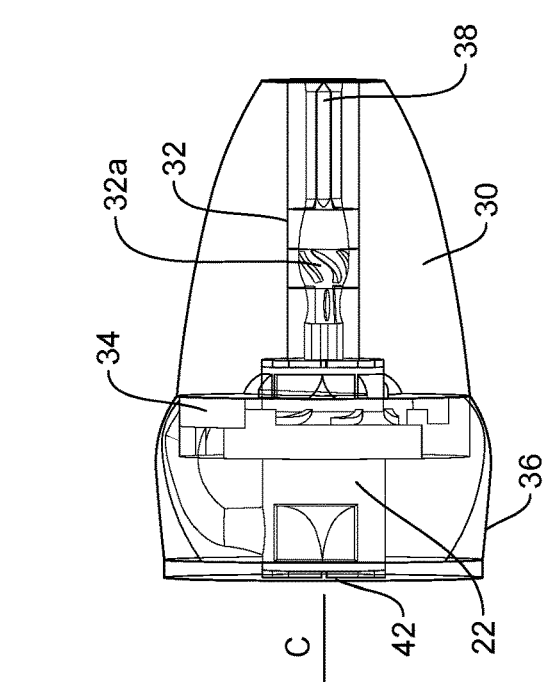

INTEGRATED ADJUSTABLE MULTI-PUMP MECHANICAL CIRCULATORY SUPPORT DEVICE

CROSS REFERENCE TO RELATED APPLICATIONS

This application claims the benefit under 35 USC § 119 (e) of U.S. Provisional Patent Application No. 62/967,865, filed Jan. 30, 2020.

BACKGROUND

Congestive heart failure (CHF) is a progressive and debilitating disease that affects more than 20 million people worldwide. In the U.S., approximately 7.5 million people suffer from CHF, and more than 650,000 new cases are diagnosed each year. This typically costs the healthcare industry about $35 billion annually, and only 2500 donor hearts are available in a typical year. Thousands are registered awaiting a donor heart; it is expected that 40% of those who are on the waiting list typically never receive a donated heart.

As a bridge-to-transplant, adult patients benefit from mechanical circulatory support (MCS) or blood pumps. For example, total artificial heart (TAH) or ventricular assist device (VAD) technology are available. Current devices have significant design limitations in short-term and long-term implementation due to physiologic challenges, such as high risk of hemorrhagic stroke, thromboembolic events, and neurologic impairment. Infection is also a high risk due to the bulkiness of the device and due to percutaneous driveline access site in the abdomen, which may stimulate significant local or systemic immune response. Conventional device designs may also limit ambulation by having a large drive console or a heavy portable unit; it is well known that patient ambulation correlates to better outcomes and overall survival rates. Other limitations of existing TAHs include risk of membrane rupture and premature mechanical/biological valve failure in pulsatile devices, higher power consumption as compared to VADs, and size constraints due to bulkiness. These limitations significantly elevate the failure risk for patients and create extensive treatment challenges for clinical teams caring for adults with CHF.

Similar to adults, children with CHF are at high-risk. Each year more than 40,000 U.S. babies are born with a congenital heart defect, and approximately 30% of these infants require surgery within the first days-to-years of life. While these children will benefit in the short-term, a growing segment with complex heart defects ultimately develop CHF, often due to complications from cardiac arrhythmias, defects, or bacterial or viral infections that attack the heart's muscle and impair its ability to effectively pump blood. Heart transplantation, when available, becomes the only lifesaving option.

Children may benefit from short-term MCS in the form of a TAH or VAD, i.e., a medical device designed to assist the heart's left ventricle (pumping blood to the body) or the heart's right ventricle (pumping blood to the lungs). However, VAD and TAH technology for children severely lags behind that for adults. While many intended-for-adult devices have been utilized in children, the operation of these pumps at off-design pressures and flows increases the potential for irregular blood flow, contributing to harmful hemolysis (blood cell rupture) and dangerous thrombosis (clotting).

Accordingly, there is an unmet need for new devices that will support the anatomic and physiological heterogeneity of childhood heart disease and the increased cardiovascular demands of physical growth in children and adolescents. In addition, there is an unmet need for a pediatric VAD with the design innovation to support a wide range of dysfunctional states of heart failure. The need is compelling because the use of existing technology for children has, in addition to the risk of hemolysis and thrombosis, numerous limitations, including bulkiness, mechanical failure of moving parts, power consumption and heat generation. Moreover, existing devices cannot support the anatomic and physiological heterogeneity of childhood heart disease and cannot adapt to patient size ranges, nor to the increased cardiovascular demands of physical growth.

BRIEF DESCRIPTION OF THE DRAWINGS

Various features of the embodiments described in the following detailed description can be more fully appreciated when considered with reference to the accompanying figures, wherein the same numbers refer to the same elements.

FIGS. 1-3 are side elevational and plan views of a mechanical circulatory support device in accordance to a parallel pump configuration embodiment.

FIGS. 4-6 are side elevational and perspective views of a mechanical circulatory support device in accordance to a series pump configuration embodiment.

DETAILED DESCRIPTION

Figure 7:
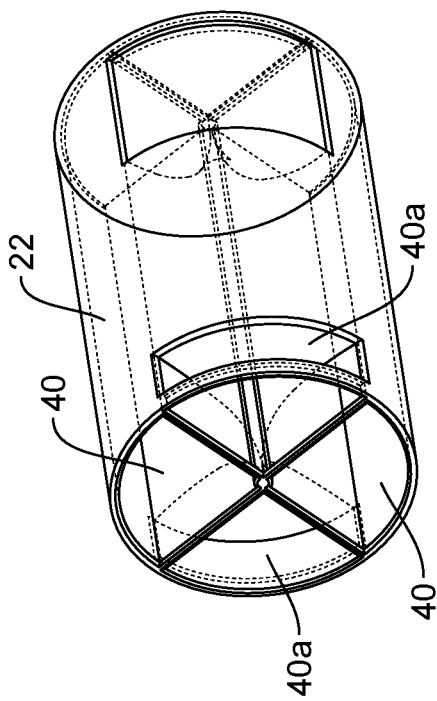
FIGS. 7-10 are perspective, plan, and side elevational views of a rotatable switching mechanism in accordance to an embodiment.
Figure 9:
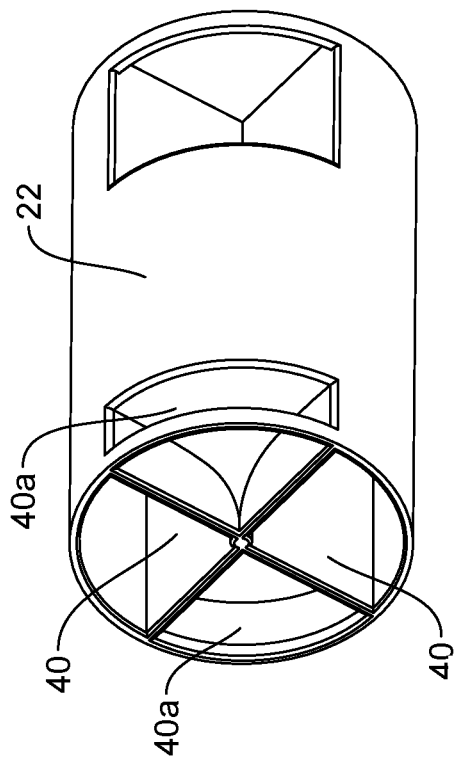
Figure 8:
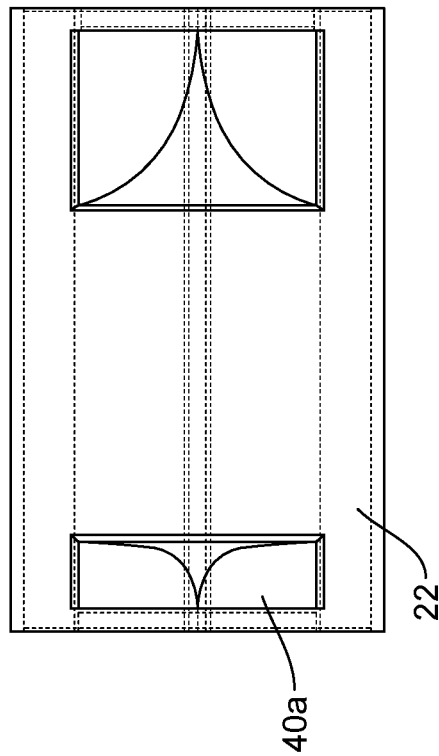
Figure 10:
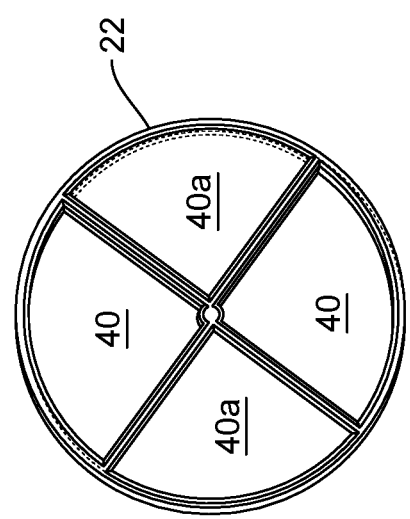
Figure 13:
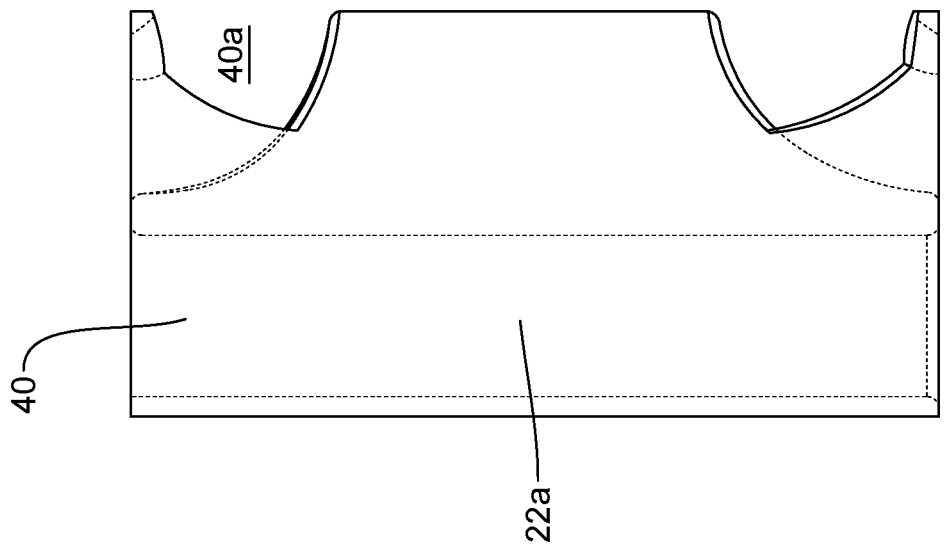
FIGS. 11-13 are perspective, plan, and side elevational views of an alternate rotatable switching mechanism in accordance to an embodiment.
Figure 11:
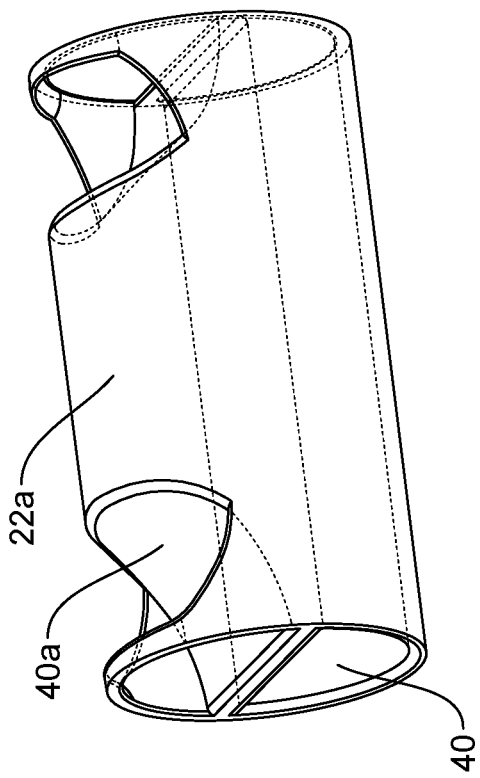
Figure 12:
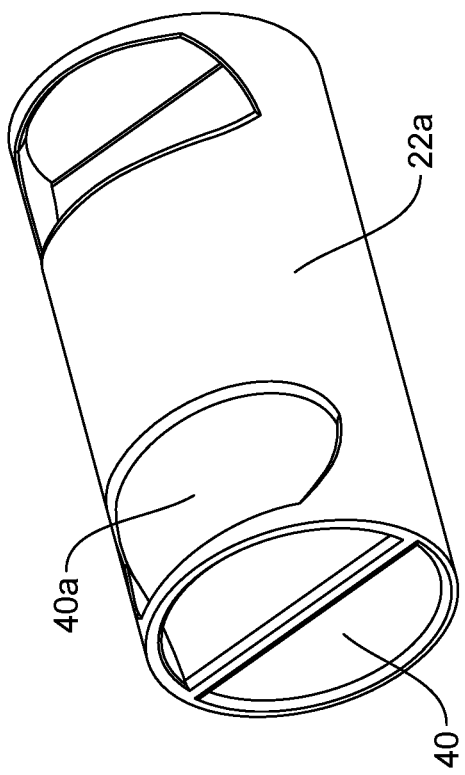
Figure 16:
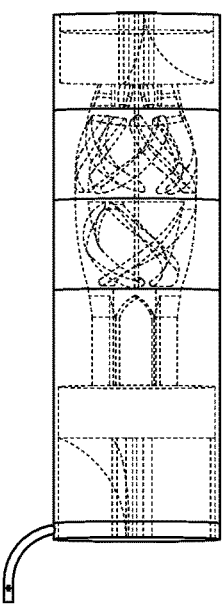
FIGS. 14-19 are plan and side elevational views of a system for rotating a switching mechanism in accordance to an embodiment.
Figure 19:
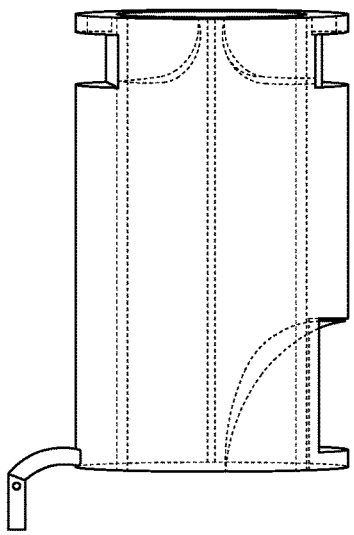
Figure 15:
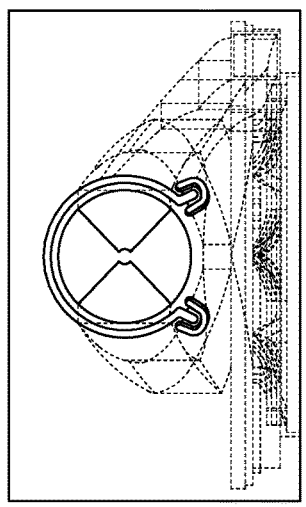
Figure 18:
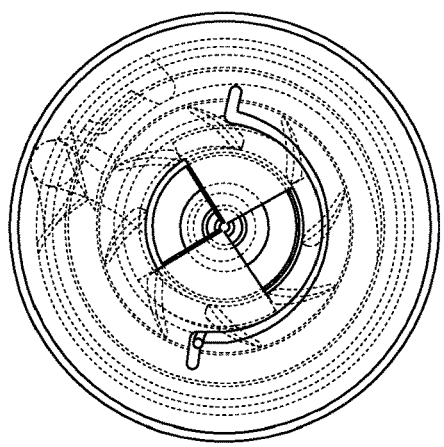
Figure 14:
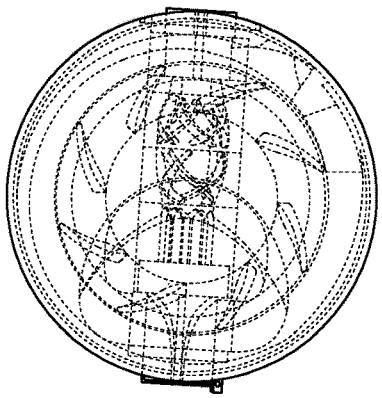
Figure 17:
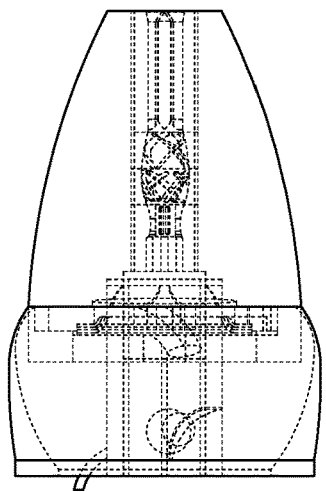
Figure 22:
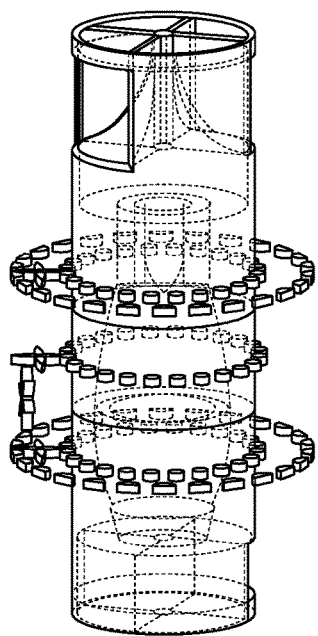
FIGS. 20-25 are plan, side elevational, and perspective views of an alternate system for rotating a switching mechanism in accordance to an embodiment.
Figure 25:
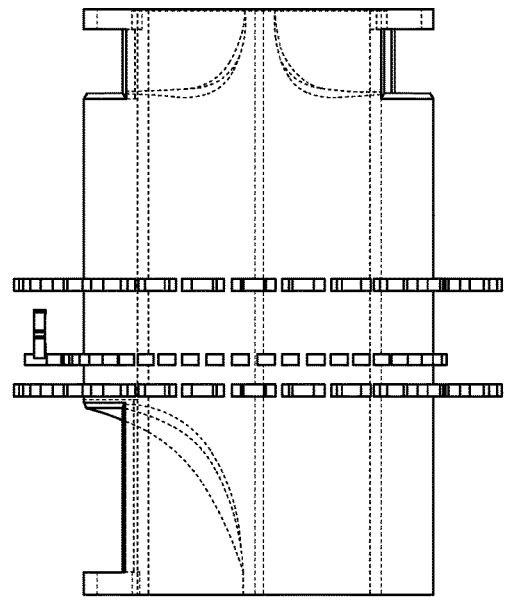
Figure 21:
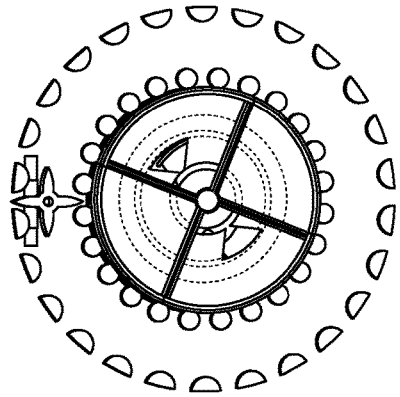
Figure 24:
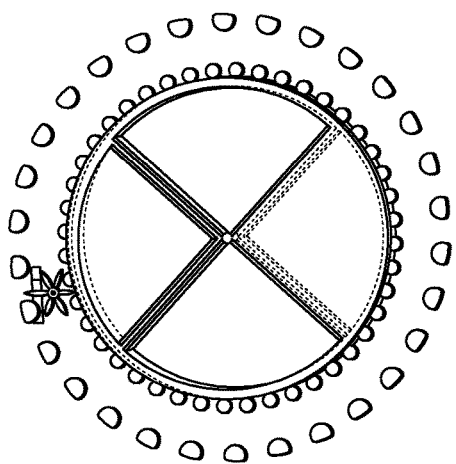
Figure 20:
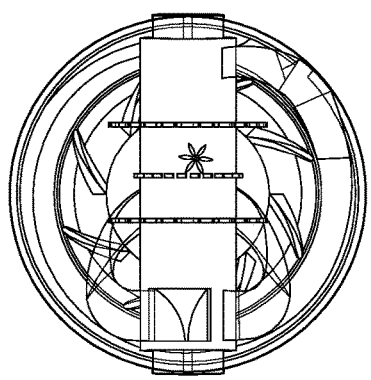
Figure 23:
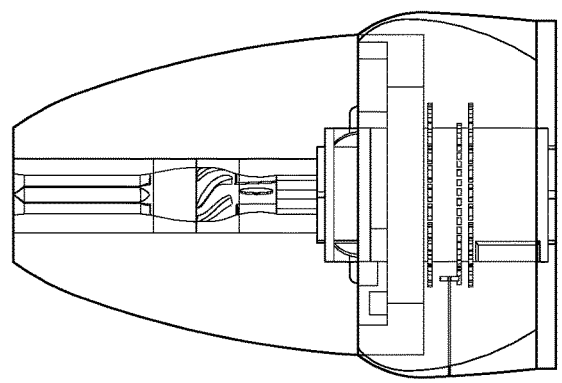
Figures 26, 27, 28:
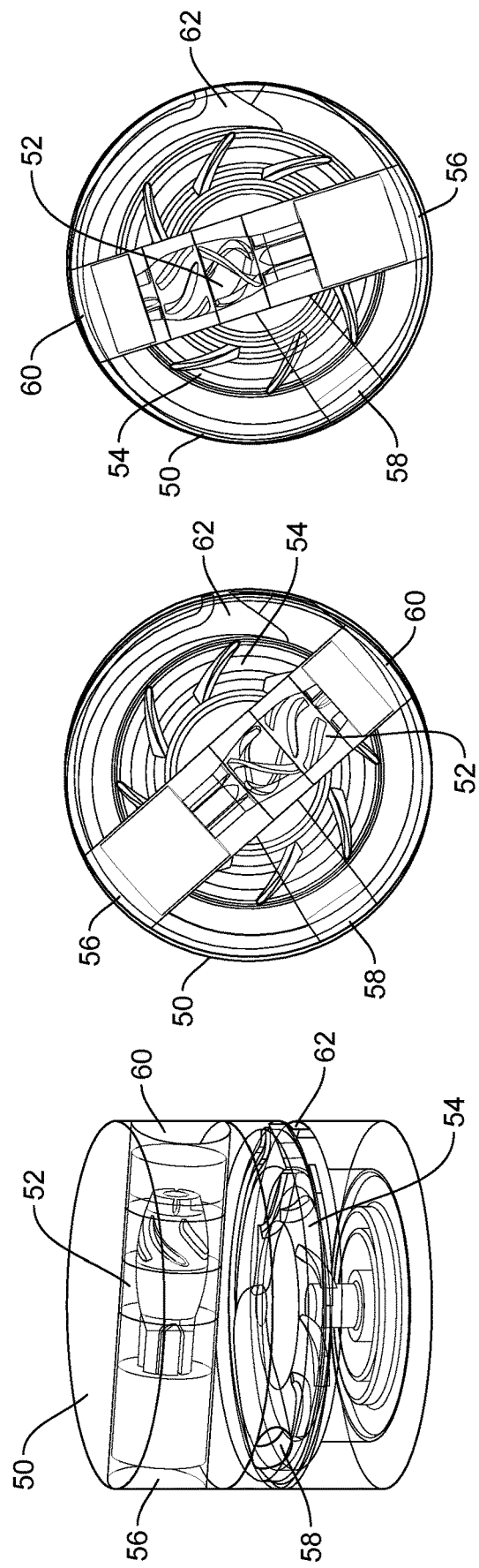
FIGS. 26-30 are perspective, plan, and side elevational views of a bi-ventricular assist device (Bi-VAD) or total artificial heart (TAH) in accordance to an embodiment.
Figure 30:
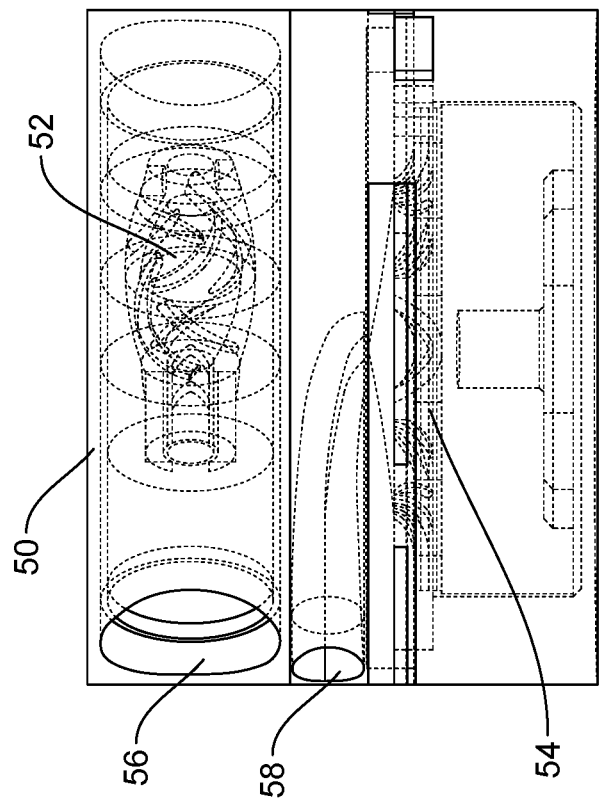
Figure 29:
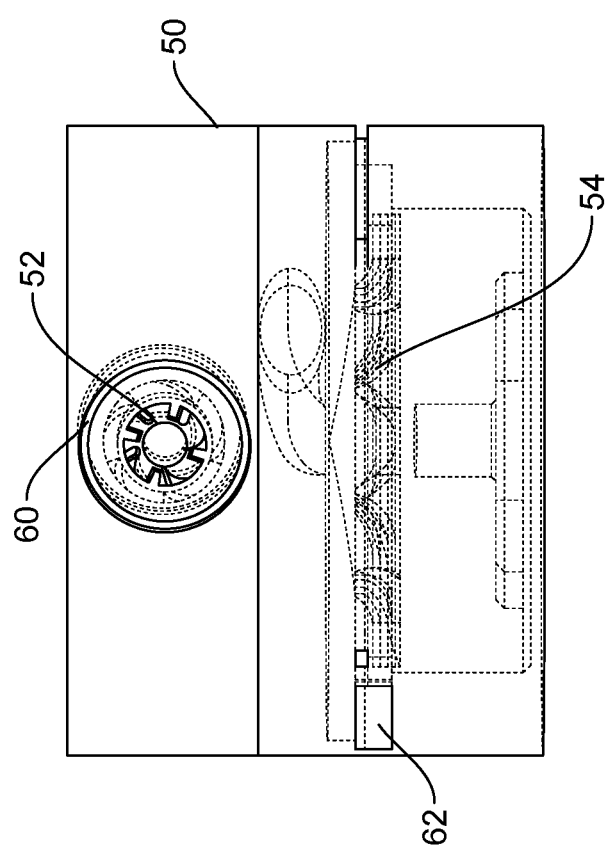

For simplicity and illustrative purposes, principles of embodiments are described below by referring primarily to examples thereof. In the following description, numerous specific details are set forth to provide a thorough understanding of the embodiments. It will be apparent to one of ordinary skill in the art that the embodiments may be practiced without limitation to these specific details. In some instances, well known methods and structures have not been described in detail so as not to unnecessarily obscure the embodiments.

According to embodiments disclosed herein, a medical mechanical circulatory support device is provided that orients two pumps, such as two different continuous-flow blood pumps (for instance, axial and centrifugal pumps), that are designed based on anatomic and physiologic cardiovascular requirements of children, adolescents, and/or adults with heart failure. According to embodiments, the two blood pumps have only two moving parts (the impellers) (i.e., an axial impeller and a centrifugal impeller). The two continuous-flow blood pumps may incorporate magnetic, mechanical, ceramic, fluid, and/or hydrodynamic bearings with a motor drive system to induce rotation and impart energy to the blood.

The dual-configured mechanical blood pumping device having only two moving parts has the versatility to provide full or partial cardiovascular support to the right, left, or both ventricles of pediatric patients. The device can not only support pediatric patients, but also their development. The device may have the ability to switch from an axial pump to a centrifugal pump, as the patient ages or as the pressure/flow demands increase. The dimensions of the device may be small enough to accommodate patients ages 5 and older. The device may be designed to utilize the latest in magnetic bearing technology to levitate the impeller, extending the operational lifespan. By way of example, the device may deliver blood flows of 1-5 L/min and generate blood pressures of 50-120 mmHg at 2,000-15,000 RPM. The rotating impellers may be levitated using magnetic bearings and rotated by permanent magnets from the motor. The innovative switching capability extends the life span of the device and allows it to support growth and development from child to adult.

Embodiments disclosed herein include two different orientations/arrangements of pumps, one in which the pumps are configured to be in parallel (see FIGS. 1-3) and the other in which the pumps are configured in series (see FIGS. 4-6). In each of these embodiments, the pumps include an axial flow pump and a centrifugal pump.

Embodiments in which the pumps are in a parallel relation comprise a mechanical circulatory support device 10 having an axial pump 12 with an axial impeller with a rotational axis "A" and a centrifugal pump 14 with a centrifugal impeller 14a with a rotational axis "B". In this embodiment the rotational axes, "A" and "B", are perpendicular with respect to each other. Of course, they could be transverse or at an angular relation.

In this configuration, the pumps, 12 and 14, are located within a single compact housing 16 which is generally disc-shaped as shown in FIGS. 1-3. The same inlet and outlet flow regions, 18 and 20, of the housing 16 are shared by the pumps, 12 and 14. As one example (see FIGS. 1-3), the axial pump 12 may be located directly above the centrifugal pump 14. The inlet 18a of the axial pump 12 connects to or is adjacent to the inlet 18b of the centrifugal pump, and, likewise, the outlet 20b of the centrifugal pump 14 connects to the outlet region 20a of the axial pump 12.

A switching mechanism, such as switching mechanism 22 shown in FIGS. 7-10, may be used to direct flow into the inlet 18a of the axial pump 12 and block flow into the inlet 18b of the centrifugal pump 14 when oriented in a first position. However, when the switching mechanism 22 is rotated about its longitudinal axis, it diverts blood flow from entering the axial pump 12 to entering the inlet 18b of the centrifugal pump 14. The switching mechanism 22 may also automatically align the outlet with the inlet, such that flow into one pump region leads to successful outflow from the pump.

FIGS. 7-10 and 11-13 show two different embodiments of a switching mechanism, 22 and 22a. Both include a generally cylindrical outer wall and define passages therein and therethrough such that flow may be directed to or blocked from a particular inlet of a pump or out of a particular outlet of a pump. For instance, each of the switching mechanisms, 22 and 22a, may have flow bypass passages 40 and flow diverting passages 40a. For instance, in the first position in device 10, the switching mechanism may direct flow into the bypass passage 40 into the axial pump and block flow to the centrifugal pump. However, in the second position in device 10, the switching mechanism 22 may divert flow with the flow diverting passage 40a into the centrifugal pump and block flow through the axial pump. Of course, a switching mechanism (not shown) could be designed to split the flow with some predetermined amount of flow in each pump.

According to an embodiment, flow can be diverted by rotating the switching mechanism, 22 or 22a, about its longitudinal axis from the first position to the second position so that the flow diverting passages 40a provided by the switching mechanism, 22 or 22a, is appropriately rearranged relative to the stationary pumps. The difference between switching mechanism 22 and 22a is that switching mechanism 22 has passages divided up by quadrants while switching mechanism 22a has passages on opposite longitudinally extending halves of the cylindrical housing.

In contrast to the parallel configuration of pumps shown in FIGS. 1-3, a series configuration of a mechanical support device 30 shown in FIGS. 4-6 integrates an axial pump 32 having an axial impeller 32a and a centrifugal pump 34 having a centrifugal impeller 34a in series along their rotational axis "C", which is the same for both. Both pumps, 32 and 34, are located within a shared compact housing 36. In this configuration, the axial pump 32 may be positioned first in-line for blood flow before the centrifugal pump 34. Flow enters the axial pump 32 at inlet 38, wherein the blood receives a pressure boost by the axial pump 32, and then the blood flows into the centrifugal pump 34, wherein it may receive another pressure boost before existing the device 30 at outlet 42.

According to an embodiment, the impeller 34a of the centrifugal pump 34 may be activated, such as when additional pressure boost is required to support the capacity and pressure needs of the patient. For instance, in some conditions, only the axial pump 32 may drive blood flow through the device 30, in some conditions only the centrifugal pump 34 may drive blood flow through the device 20, and/or in some conditions, both pumps, 32 and 34 may drive blood flow through the device 30.

A switching mechanism, 22 or 22a, may be used to enable activation of the centrifugal pump 34 and to ensure that blood exits the axial pump 32 and flows through the centrifugal pump 34. The switching device, 22 or 22a, could also be used to block blood flow from the axial pump 32 into the centrifugal pump 34 so that blood flow bypasses the centrifugal pump 34 and passes through the bypass passage 40 within the switching device, 22 or 22a, to the outlet 42. For instance, see bypass passage 40 in switching device, 22 or 22a. Thus, by rotating the switching device within the device 30, blood flow may either be diverted into the centrifugal pump 34 from the axial pump 32 or may bypass the centrifugal pump 34 through the bypass passage 40 of the switching device depending upon the rotational alignment of the switching device within the device 30 relative to the pumps, 32 and 34.

Both of the series and parallel embodiments include a housing, 16 and 36, which is fixed and has an inlet and an outlet that can be directly connected to the ventricles, aorta, pulmonary artery, vena cavae, or other cardiovascular vessels via cannulae connections. The drive components of the impellers of the pumps and the switching components may be achieved by several mechanisms utilizing bearings, wheels, gears, high density and viscosity fluids, magnetism, crank, and/or spool/wiring located within the housing.

These embodiments provide a blood pump that has the ability to switch from one type of blood pump to another, for instance, by rotating a component (i.e., the switching mechanism, 22 or 22a) about a single axis. These embodiments facilitate a miniature configuration that can provide mechanical circulatory support to children, adolescents, and adults. Thus, the embodiments address an unmet clinical need for new medical devices that support the anatomic and physiological heterogeneity of childhood heart disease and the increased cardiovascular demands of physical growth in children and adolescents. In addition to providing the necessary pressure and flow requirements for children, adolescents, and adults with CHF, the switching mechanism provides an opportunity for the patient to switch to and be supported by a new or different blood pump without having an open-heart medical procedure.

The embodiments discussed above may provide one or more of the following distinctive design attributes.

Hybrid Design: These embodiments may incorporate both an axial and centrifugal pump in a parallel or series configuration within a single, compact pump housing. The pumps may provide different pumping characteristics. Thus, for instance, as a child grows and his/her blood flow requirements change, a switch to a different one to both pumps may be accomplished in vivo.

Few Moving Parts: These pumps have only two moving parts—an axial impeller and a centrifugal impeller. The use of mechanical/biologic valves that may prematurely fail due to repetitive opening/closings is avoided, thus minimizing thrombosis risk.

Dual-Support Feature: These embodiments have the capability of producing continuous or pulsatile blood flow through specialized control algorithms. During longer-term mechanical circulatory support, pulsatile flow may be desirable to alleviate bleeding that may develop in the digestive track due to von-Willebrand cleaving.

Combined Motor-Bearing: These embodiments may utilize magnetic bearings to levitate the impellers in a magnetic field, thus facilitating a longer operational lifespan (for instance, 10-15 years) and wider clearances between the rotating and stationary surfaces, which lower fluid stresses and reduce thrombosis and hemolysis. Other bearing components, such as mechanical, fluid, ceramic, and/or hydrodynamic bearings could be used and integrated into the embodiments.

Wireless Power System: A wireless energy transfer system may be implemented into the embodiments to eliminate commonly deployed hardline connections through the abdomen. The transfer system may incorporate self-monitoring with Wi-Fi sensors. Lightweight materials as wearable drive components (e.g. batteries) may be utilized.

Excellent Biocompatibility: By using the latest generation of magnetic suspension, these embodiments will levitate and rotate the impellers that drive blood flow across biocompatible surfaces having much wider clearances, which lower fluid shear stresses and facilitates surface washing to minimize thrombosis/hemolysis.

Versatility in Therapy: These embodiments have two pumps integrated into single mechanical support device which means that this medical device (either of the disclosed series or parallel embodiments) could operate in a multitude of ways. The device could be employed to assist only the left-side of the heart or to assist only the right-side of the heart. As another alternative, a device combining a pair of the above embodiments could be provided such that the device may be used as a TAH, whereby mechanical circulatory support is provided to both the left and the right ventricles. The embodiments also allow for an operational switch from the axial to the centrifugal pump as a child grows and requires higher flows and pressures. Accordingly, this hybrid configuration may be used for high-risk pediatric and adult patients with CHF or secondary acquired or congenital heart disease.

Switching Mechanisms: Within the parallel pump embodiment, a rotating switching mechanism, 22 or 22a, for enabling a switch may be provided as a component forming part of the axial pump 12 (see FIGS. 1-3). In the series pump embodiment, the rotating component, 22 or 22a, for providing a switching mechanism may be positioned along a path of the axial pump outlet and may extend through a center of the centrifugal pump 34 (see FIGS. 4-6).

With respect to rotating the switching mechanism, 22 or 22a, about its longitudinal axis within the devices 10 and 32, various systems may be used. By way of example, and not by way of limitation. The following rotational drive features may be utilized.

Gears may be used to rotate a suspended switching mechanism, 22 or 22a, by any of the following: a cable/wire spooling system; two or three sets of wheels arranged along the length of the rotating component; two or three sets of secondary gears arranged along the length of a rotating component (see FIGS. 20-25); a rod with or without threads; a chain or belt; a removable pin that releases a set of springs; fluid driven through the movement of magnets pulled by a spooling system; electromagnetism used to rotate the switching mechanism around a single axis; double or triple spring mechanism arranged along the length of the rotating mechanism; or a disk with a rotating arm where the rotation of the disk causes the arm to rotate thus causing a secondary rotation to rotate the switching mechanism.

Alternatively, a crank, handle, or gear plus a crank may be used to: manually rotate the switching mechanism around a single axis (see FIGS. 14-19); rotate gears; rotate cable/wire spooling; rotate a chain or belt connected to a wheel; rotate a rod with or without threads; remove a pin in order to release a set of springs, such as a double or triple spring mechanism arranged along the length of the rotating component; or rotate a secondary rod connected to a rotating handle.

As another alternative, magnetic forces may be used to rotate the switching mechanism, 22 or 22a, from 0° to 360° depending on the size of the inlets/outlet openings (see FIGS. 14-19). In addition, bearings, wheels, gears, high density, and viscosity fluid, dampening cushion, and/or magnetism may be used to stabilize and maintain the rotating components of the switching mechanisms suspended and/or rotating around a single axis.

With respect to a cable/wire spooling system referenced above, one end of the cable/wire may be connected to an exterior of the rotating component and the other end may be connected to a spooling winder. The spooling system may have a handle that opens and closes and that is held in place by a magnetic socket. The magnetic socket may prevent the handle from rotating in an opposite direction. Rotation of the handle causes the cable/wire to be collected onto the winder which in turn rotates the switching mechanism along a single axis. The rotating component is held in place and stabilized by any of a sets of gears, high viscosity ferrofluid, wheels, dampening cushion, magnetism, and the like.

With respect to the two to three sets of wheels arranged along the length of the rotating component as referenced above, the rotating component may be supported by two columns of three sets of wheels. One of the wheels may be connected to a gear mechanism, cranking mechanism, gear plus crank mechanism, or a motor. Each of the three mechanism can be used to rotate one of the wheels pressed onto the rotating component. Rotation of the wheel causes the rotating component to rotate along a single axis. The other wheels act to stabilize the switching mechanism as it is rotating.

With respect to the two to three sets of gears arranged along the length of the rotating component as referenced above (see FIGS. 20-25), this type of system can be rotated along a single axis by using a crank connected to the rotating component. The crank arm opens when needed and closes into its magnetic socket after performing a rotation. The magnetic socket prevents the arm from rotating thus keeping the switching mechanism stationary. Another method for rotating one of the gears is through the use of a single isolated gear positioned perpendicular to one of the gears resting on the rotating component. The perpendicular gear is controlled through a rotation of a key. Another method is using a belt, chain, or a disk with a crank on it. These can be rotated manually through the use of a key or rotated by a miniature motor. Rotation of the belt, chain, or disk causes the gear connected to the rotating component to rotate which in turn causes the switching mechanism to rotate with respect to a single axis.

With respect to being fluid driven through the movement of magnets pulled by a spooling system, a ferrofluid (a highly magnetic fluid) may be used. The entire volume of the fluid can be pulled through the use of a magnet moving across the surface of the fluid housing. As the ferrofluid is pulled it comes into contact with an arm extruding from the rotating component. Attractive force experienced by the ferrofluid cause it to apply pressure onto the extruding arm thus rotating the switching mechanism. When the winder stops so does the magnet thus keeping the fluid locked in place near the magnet.

With respect to using electromagnetism to rotate the switching mechanism around a single axis, a short-pulsed supply of eddy current to the conductive material around the exterior of the rotating component may be utilized. Reversing the direction of the electrons causes the magnetic field to flip, thus rotating the switching mechanism. The rotating component may be housed inside two rows of electromagnets which surround the rotating component. The gap between the magnets may be filled with magnetic metals.

With respect to a double or triple spring mechanism referenced above, it may be arranged along the length of a cylinder and two or more sets of spring-loaded mechanisms may be used to make sure the switching mechanism rotates uniformly without vibrating or undergoing sudden twitching/jerking when the springs are extended. Springs may be held in place through a pin mechanism. Each pin may be directly connected to a gear, winder, or crank. Rotation of the gear, winder, and/or crank will pull out the pins at the same time and the springs will then extend in uniform. Each spring may be pushing against an extruding arm connected to the rotating component. Extension of the spring causes the switching mechanism to rotate around a single axis.

A disk with a rotating arm may also be used. The rotation of the disk causes an arm to rotate thus causing a secondary rotation. The disk can be rotated by a motor, crank, handle, and gears. As the arm rotates it may cause rotation of secondary wheels and gears connected to the rotating component.

According to embodiments a method of switching blood pumps is also provided. The method includes a process step of intentionally causing rotation of a switching mechanism within a mechanical circulatory support device, 10 or 30, that is implanted within a patient. The device, 10 or 30, is connected via cannulas to large blood vessels or ventricles of the patient, and upon activating the switching mechanism, blood flow is diverted to one of the pumps or bypassed around one or the pumps or blood flow is directed through both pumps or only a single pump.

FIGS. 26-30 illustrate an embodiment in which a pair of pumps, 52 and 54, are oriented in a parallel configuration so as to provide a Bi-VAD/TAH 50 instead of a single ventricle VAD as discussed above with respect to FIGS. 1-3. In the Bi-VAD/TAH 50 embodiment, the inlets, 56 and 58, of each of the pumps, 52 and 54, are separate, and the outlets, 60 and 62, of each of the pumps, 52 and 54, are separate. Thus, in this embodiment, the pumps render the parallel concept into a Bi-VAD (if ventricles left intact) or a TAH (if the ventricles are removed). According to an embodiment, the two halves of the Bi-VAD/TAH 50 (i.e., the two pumps, 52 and 54) can be rotated relative to each in any orientation about a single axis extending transversely therethrough as needed to properly position the inlets and outlets based on the patient's physiology.

Figure 31:
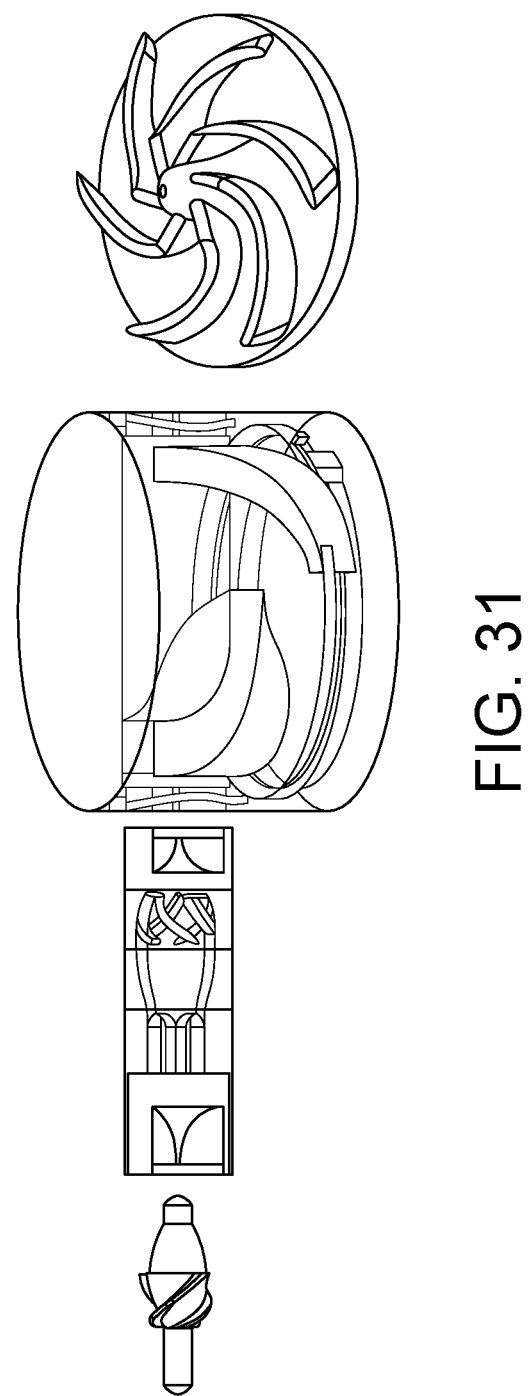
FIG. 31 is an exploded perspective view of an embodiment of an axial and centrifugal pump configuration in a single housing.

A further example of an embodiment is shown in FIG. 31. The axial pump in this embodiment may have an overall length of about 50 mm and a diameter of less than about 15 mm, and the impeller may be designed to have 4 blades. FIG. 130 illustrates the orientation of the two pumps for the hybrid concept. An axial and a centrifugal pump are positioned in parallel with respect to one another in a single housing.

The axial pump may be able to provide 50-80 mmHg for 1-3 LPM for operating speeds of 11,000 to 14,000 RPM. The average scalar stress, blood damage index, residence time, radial and axial forces may meet standard design specifications for these types of magnetically levitated blood pumps. The centrifugal pump obtained through the Taguchi Optimization method may have an overall height of 7.5 mm and diameter that is less than 50 mm. The centrifugal pump component may be able to provide 80-120 mmHg for 3-5 LPM while running at 2,500 to 3,500 RPM. The average scalar stress, blood damage index, residence time, radial forces may all be within desired limits. This innovative new medical device will offer hope for improved outcomes to the thousands of affected children and young adults with heart failure in need of life saving support, as a bridge-to-recovery, bridge-to-transplantation, or long-term therapy.

While the principles of the invention have been described above in connection with specific devices, systems, and/or methods, it is to be clearly understood that this description is made only by way of example and not as limitation. For instance, while an implantable blood pump is described above, the disclosed device may be used in any mechanical circulatory support system. In addition, the pump design may also be used for other medical and non-medical purposes.

One of ordinary skill in the art will appreciate that various modifications and changes can be made without departing from the scope of the claims below. Accordingly, the specification and figures are to be regarded in an illustrative rather than a restrictive sense, and all such modifications are intended to be included within the scope of the present invention.

We claim:
1. A mechanical circulatory support device, comprising:
a housing containing separate first and second pumps, each pump having an inlet, an outlet, and an impeller; and a switching mechanism within said housing and movable from a first position to a second position to divert blood flow within said housing to one of said pumps or to bypass blood flow relative to one of the pumps within the housing;

wherein, in the first position, the switching mechanism directs blood flow through the first pump and not the second pump, and wherein, in the second position, the switching mechanism directs blood flow through the second pump and not the first pump; and wherein the first and second pumps include a centrifugal pump and an axial flow pump.

2. The mechanical circulatory support device according to claim 1, wherein the inlet and the outlet of the first pump and the inlet and the outlet of the second pump are arranged such that the switching mechanism in the first position diverts blood flow into the axial flow pump and blocks blood flow into the centrifugal pump and such that the switching mechanism in the second position diverts blood flow into the centrifugal flow pump and blocks blood flow into the axial flow pump.

3. The mechanical circulatory support device according to claim 2, wherein the inlet and the outlet of the first pump and the inlet and the outlet of the second pump are arranged in a parallel configuration.

4. The mechanical circulatory support device according to claim 1, wherein the switching mechanism defines a blood flow diverting passage and a separate bypass passage.

5. The mechanical circulatory support device according to claim 4, wherein the switching mechanism has a longitudinal axis and is rotatable about said longitudinal axis for being repositioned from said first position to said second position.

6. The mechanical circulatory support device according to claim 5, further comprising means for rotating the switching device from the first position to the second position.

7. A method of switching pumps, comprising the step of activating the switching mechanism of the mechanical circulatory support device according to claim 1 connected via cannulas to large blood vessels or ventricles of a patient, and upon activating the switching mechanism, blood flow is diverted from the inlet of the first pump within the device to the inlet of the second pump within the device.

8. The method according to claim 7, wherein during said activating step the switching mechanism is caused to be rotated within and relative to the housing.

9. A mechanical circulatory support device, comprising:
a housing containing separate first and second pumps, each pump having an inlet, an outlet, and an impeller; and a switching mechanism within said housing and movable from a first position to a second position to divert blood flow within said housing to one of said pumps or to bypass blood flow relative to one of the pumps within the housing;

wherein, in the first position, the switching mechanism directs blood flow exiting the first pump into a bypass passage so that blood flow bypasses the second pump, and wherein, in the second position, the switching mechanism directs blood flow exiting the first pump into the second pump; and wherein the first and second pumps include a centrifugal pump and an axial flow pump.

10. The mechanical circulatory support device according to claim 9, wherein the inlet and the outlet of the first pump and the inlet and the outlet of the second pump are arranged such that the switching mechanism in the first position diverts blood flow exiting the axial flow pump into a bypass passage to bypass flow into the centrifugal pump and such that the switching mechanism in the second position diverts blood flow exiting the axial flow pump into the inlet of the centrifugal flow pump.

11. The mechanical circulatory support device according to claim 10, wherein the inlet and the outlet of the first pump and the inlet and the outlet of the second pump are arranged in series.

12. The mechanical circulatory support device according to claim 9, wherein the switching mechanism defines a blood flow diverting passage that is separate from the bypass passage.

13. The mechanical circulatory support device according to claim 12, wherein the switching mechanism has a longitudinal axis and is rotatable about said longitudinal axis for being repositioned from said first position to said second position.

14. The mechanical circulatory support device according to claim 13, further comprising means for rotating the switching device from the first position to the second position.

15. A method of switching pumps, comprising the step of activating the switching mechanism of the mechanical circulatory support device according to claim 9 connected via cannulas to large blood vessels or ventricles of a patient, and upon activating the switching mechanism, blood flow is diverted from the outlet of the first pump within the device to the inlet of the second pump within the device.

16. The method according to claim 15, wherein during said activating step the switching mechanism is caused to be rotated within and relative to the housing.

* * * * *